(12) United States Patent
Pauser et al.

(10) Patent No.: US 7,963,937 B2
(45) Date of Patent: Jun. 21, 2011

(54) SYRINGE FOR A MULTI-COMPONENT PASTE

(75) Inventors: Helmut Pauser, Diessen (DE); Michael Knee, Peiβenberg (DE); Ingo W. Wagner, Wörthsee (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 11/570,001

(22) PCT Filed: Jun. 3, 2005

(86) PCT No.: PCT/EP2005/005985
§ 371 (c)(1),
(2), (4) Date: Nov. 7, 2007

(87) PCT Pub. No.: WO2005/118154
PCT Pub. Date: Dec. 15, 2005

(65) Prior Publication Data
US 2008/0195082 A1    Aug. 14, 2008

(30) Foreign Application Priority Data
Jun. 4, 2004    (EP) .................................... 04013271

(51) Int. Cl.
*A61M 5/00* (2006.01)
*A61M 5/315* (2006.01)
*A61M 37/00* (2006.01)
*B67D 7/74* (2010.01)
*B67D 7/78* (2010.01)
*B01F 15/02* (2006.01)

(52) U.S. Cl. .......... 604/82; 604/181; 604/187; 604/191; 604/218; 604/236; 604/89; 604/90; 222/129; 222/145.1; 222/145.5; 366/177.1; 366/178.1

(58) Field of Classification Search .................. 222/129, 222/135, 137, 145.1, 145.5, 145.6; 366/177.1, 366/178.1; 604/181, 187, 191, 218, 518, 604/82, 83, 89, 91, 236, 500, 90
See application file for complete search history.

(56) References Cited

U.S. PATENT DOCUMENTS

| | | | | | |
|---|---|---|---|---|---|
| 4,655,747 | A | * | 4/1987 | Allen, Jr. ........................ | 604/89 |
| 4,690,306 | A | * | 9/1987 | Staheli ............................ | 222/80 |
| 4,767,026 | A | * | 8/1988 | Keller et al. ................... | 222/137 |
| 5,080,262 | A | * | 1/1992 | Herold et al. ................. | 222/135 |
| 5,354,264 | A | * | 10/1994 | Bae et al. ........................ | 604/21 |
| 5,386,928 | A | * | 2/1995 | Blette ............................. | 222/94 |
| 5,401,246 | A | * | 3/1995 | Mazur et al. .................. | 604/110 |
| 5,562,624 | A | * | 10/1996 | Righi et al. .................... | 604/110 |
| 5,722,829 | A | * | 3/1998 | Wilcox et al. .................. | 433/90 |
| 6,302,574 | B1 | * | 10/2001 | Chan .......................... | 366/160.4 |
| 6,613,021 | B2 | * | 9/2003 | Sogaro ........................... | 604/191 |
| 6,705,756 | B2 | * | 3/2004 | Botrie et al. ............. | 366/181.5 |
| 7,306,126 | B2 | * | 12/2007 | Brugner ....................... | 222/485 |
| 2002/0087122 | A1 | * | 7/2002 | Sogaro ........................ | 604/191 |
| 2007/0156102 | A1 | * | 7/2007 | Py .................................. | 604/218 |

FOREIGN PATENT DOCUMENTS
EP    0 747 114 A1    12/1996

* cited by examiner

*Primary Examiner* — Kevin C Sirmons
*Assistant Examiner* — Shefali D Patel

(57) ABSTRACT

The present invention relates to a syringe for storage, mixing and dispensing of multi-component paste materials, and more precisely to a syringe for two or more components of a paste material which are to be mixed together. The syringe may be activated so that the chambers containing the components are opened, and the components may be mixed together and extruded through a mixing tip.

23 Claims, 7 Drawing Sheets

SYRINGE FOR A MULTI-COMPONENT PASTE

This application is the U.S. national stage application of International Application PCT/EP2005/005985, filed Jun. 3, 2005, which international application was published on Dec. 15, 2005, as International Publication WO/2005/118154 in the English language. The International Application claims priority of European Patent Office Application 04013271.4, filed Jun. 4, 2004.

BACKGROUND OF THE INVENTION

1. Technical Field

The present invention relates to a syringe for storage, mixing and dispensing of multi-component paste materials, and more precisely to a syringe for two or more components of a paste material which are to be mixed together.

2. Description of the Related Art

Known syringes require an activation step, disassembly/assembly of parts and usually they do not provide a complete extrusion of the paste.

U.S. Pat. No. 6,613,021 describes an ampoule for dispensing a substance or a mixture of a plurality of substances. One embodiment of this ampoule (shown, for example, in FIGS. 15 and 16 of this document) comprises a container with two chambers being arranged in parallel, i.e., not concentrically. At the front end of the container, an annular neck is formed. This neck surrounds outlet openings of the two chambers and receives an outlet piece defining a mixing space. In the transport and storage condition of the ampoule, the outlet piece is inserted into the annular neck of the flange but substantially spaced from the outlet openings of the two chambers. In this space formed within the annular neck between the outlet piece and the outlet openings of the chambers, a multiplug-closure means is located. In other words, the closure means is located outside of the component chambers downstream of the outlet openings. The closure means comprises two cylindrical plug portions that close the outlet openings. That means, for each chamber a separate plug is provided. For activating the ampoule, the outlet piece is inserted into neck, i.e., pushed towards the chambers. This displacement of the outlet piece also displaces the closure means so that the two plug portions clear the outlet openings of the chambers. The substances contained in the chambers can escape through the outlet openings and through through-holes on the closure means into the mixing space in the outlet piece. Thus, the ampoule of U.S. Pat. No. 6,613,021 requires manual activation by pushing the outlet piece to displace the closure means, and requires displacement of the outlet piece and closure means opposite to the direction of movement of the plungers.

EP-A-0 747 114 relates to prepackaging of bone cements in the form of two liquid components. According to one embodiment, a dual compartment container having two concentric chambers is suggested. The two concentric chambers are closed at their front ends by a single thin, air impermeable sealing layer.

SUMMARY OF THE INVENTION

The present invention provides a three-step function of the plunger or piston assembly whereas switching from the first to the third step occurs automatically and during an "all in one" movement. In the first step the syringe is activated which means that the chambers containing the paste components are opened. In the second step the paste components are extruded through a mixing tip containing a static mixer and through a dispensing nozzle. Finally, in the third step, the mixer is compressed to extrude all the remaining paste out of the mixing tip.

The present invention provides a syringe for two or more components of a material which are to be mixed together, comprising:
  a first component chamber for containing a first component and a second component chamber for containing a second component, each component chamber comprising a chamber outlet;
  a first piston for movement within the first component chamber and a second piston for movement within the second component chamber;
  a plug comprising a first flow channel for the first component and a second flow channel for the second component, the plug being movably arranged in the first component chamber in such a manner that when the plug is in a first position, the chamber outlets are closed and when the plug is in a second position, the first and the second component chambers are connected to the outlet of the syringe via the first and the second flow channels.

In other words, the present invention relates to a syringe for two or more components of a material which are to be mixed together, comprising:
  a first component chamber for containing a first component and a second component chamber for containing a second component, each component chamber comprising a chamber outlet;
  a first piston for movement within the first component chamber and a second piston for movement within the second component chamber;
  a mixing tip comprising a front end with a dispensing opening and a rear end with an inlet opening, the rear end being connected to the chamber outlets;
  a static mixer arranged in the mixing tip;
  a plug comprising a first flow channel for the first component and a second flow channel for the second component, the plug being movably arranged in the first component chamber in such a manner that when the plug is in a first position, the chamber outlets are closed and when the plug is in a second position, the inlet opening of the mixing tip is connected via the first and the second flow channels to the first and the second chamber outlets respectively.

It may be provided that the first component chamber is concentrically arranged inside the second component chamber.

Preferably, the first flow channel is formed by a first channel portion and a second channel portion separated from each other by a separation wall. It is also preferred that the first component chamber comprises at its front end a recess in the inner surface thereof. The first and second channel portions of the first channel then form a flow path with the first component chamber recess in the second position of the plug.

The second chamber outlet is preferably located at the front end of the second component chamber and extends from the second component chamber to the first component chamber. The second component chamber may further comprise at its front end an inlet from the exterior of the syringe.

The first piston preferably comprises a recess in a middle area of its length. The first piston recess is preferably in the form of an annular groove (of a rectangular section or profile) in a plane substantially perpendicular to the longitudinal axis of the first piston.

The second piston preferably comprises at least one engagement projection at its back end, wherein the engagement projection protrudes towards the center axis of the second piston so as to enable engagement with the annular groove of the first piston.

The engagement projection is for example formed as a spring sleeve. The second piston may also comprise a weakened area such as an annular recess near to its back end. Such weakened area allows deflection of the engagement projection. Preferably, the back end of the second component chamber is at its outer edge conically shaped in order to allow such deflection.

According to a preferred embodiment of the present invention, the second component chamber comprises one or more separation walls extending in longitudinal direction of the syringe thus dividing the second component chamber into two or more sub-chambers. Preferably, the second component chamber comprises two or four separation walls equally spaced from each other.

It is also preferred that the syringe according to the present invention comprises a mixing tip having a front end with a dispensing opening and a rear end with an inlet opening. Preferably, the mixing tip when connected to the component chambers covers and seals the inlet formed in the second component chamber. It is also preferred that a static mixer is in the mixing tip.

According to a further aspect of the present invention, a method of filling a syringe is provided comprising the steps of: filling the first component chamber with the first component; inserting the plug into the first component chamber from the front end thereof; and filling the second component chamber with the second component.

According to a further aspect, the present invention provides a method of mixing and dispensing of multi-component paste materials using a syringe according to the present invention, comprising the steps of: a) activating the syringe and opening the chambers containing the paste components; b) extruding the paste components from the component chambers through outlets into a mixing tip containing a static mixer; and c) extruding paste remaining in the mixing tip by compressing of the static mixer.

Thus, the present invention preferably relates to a concentric arrangement of the paste chambers and a closure plug which interact in a manner that only one plug is used to seal all chambers to encapsulate the stored pastes and to open all chambers at the same time when it is displaced. An advantage of the concentric arrangement of the chambers is the potential to easily make a syringe for multi-component pastes as well as for two-component and multicomponent pastes without changing the syringe design.

The present invention provides the advantage that no activation or other preparation step is necessary prior to use and at the same time the syringe allows complete extrusion of the paste by collapsing the mixer. Activation, mixing and paste extrusion as well as collapsing the mixer can be done in an all in one movement. Furthermore the length of the syringe is within usual dimensions of syringes which have proven for optimum handling.

BRIEF DESCRIPTION OF THE DRAWINGS

The present invention will now be described with reference to the accompanying drawings, in which:

FIG. 2b shows another perspective view of the plug of FIG. 2a;

DETAILED DESCRIPTION OF PREFERRED EMBODIMENTS

Figure 1:
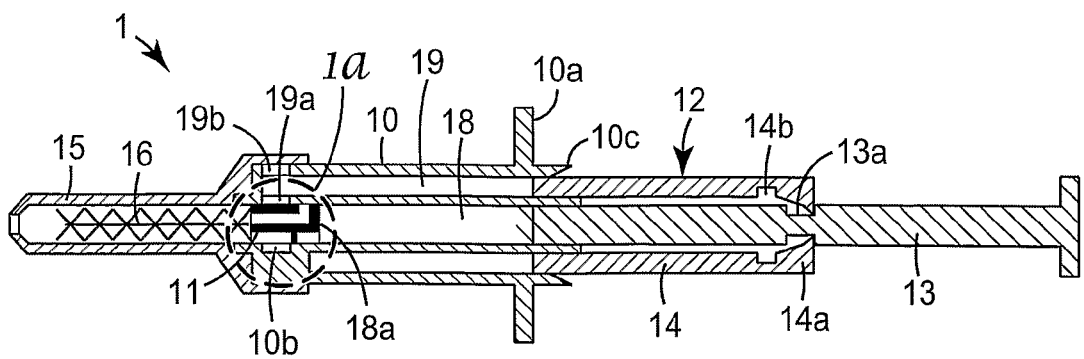
FIG. 1 shows a cross sectional view of a syringe according to a preferred embodiment of the present invention.

Preferred embodiments of the invention are described in more detail below with reference to the attached drawings, which are by way of example only.

In a preferred embodiment as shown in FIGS. 1 to 4, a syringe 1 comprises a cartridge 10, a plug 11, a piston assembly 12 with an inner piston 13 and an outer piston 14, and a mixing tip 15 with a static mixer 16.

The cartridge comprises a first component chamber 18 and a second component chamber 19. Preferably, the two component chambers are arranged concentrically, i.e. the first component chamber 18 being concentrically arranged inside the second component chamber 19. The inner piston 13 is moveable in the first component chamber 18, and the outer piston 14 is moveable in the second component chamber 19.

As shown in detail in FIG. 1, the inner piston 13 is preferably substantially cylindrical but comprises a recess, for example an annular groove 13a, approximately in the middle of the length of the piston 13. Preferably, the annular groove 13a lies in a plane perpendicular to the longitudinal axis of the inner piston. This recess 13a cooperates with engagement projections (for example a spring sleeve 14a) formed at the back end of the outer piston 14. This engagement functionality provides plunger assembly 12. The engagement projections 14a preferably project towards the center axis of the outer piston 14, i.e., towards the inner piston 13. The engagement of the outer piston 14 with the inner piston 13 is described in more detail below with reference to FIGS. 16 to 20.

At the back end of the cartridge 10, one or more projections are formed being perpendicular to the longitudinal axis of the cartridge 10. Preferably, as shown in FIG. 1, an annular projection 10a is provided. The user can easily grasp and hold the syringe at this projection, especially when applying pressure on the plunger assembly 12 to dispense material from the syringe 10.

At the front end of the cartridge 10, the first and second component chambers 18, 19, comprise outlets. The first component chamber 18 comprises outlet 18a at the front end of the component chamber, i.e., in axial direction. On the other hand, the second component chamber 19 comprises a radial outlet 19a towards the center of the cartridge 10, i.e., towards the first component chamber 18. In this area, the cartridge comprises a recess 10b in the inner surface of the cartridge 10 facing the first component chamber 18. Furthermore, an opening 19b in radial direction is provided in the cartridge wall connecting the second component chamber 19 with the exterior of the syringe 10. This opening 19b is preferably used for filling the second component chamber 19 from the outside and facilitates molding of the recess 19a. As shown in FIG. 1 this fill opening 19b is covered and sealed by the back end of the mixing tip 15, for example by an annular flange, once the second component chamber 19 is filled.

Figure 1A:
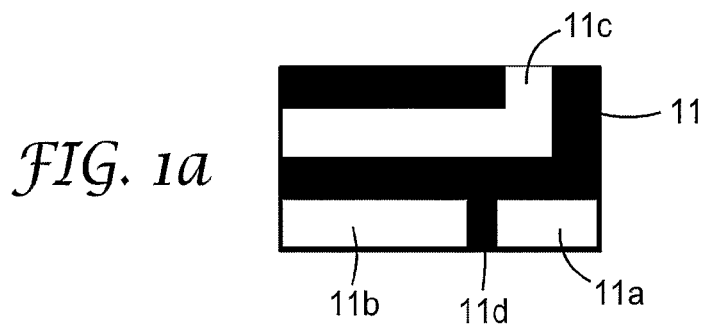
FIG. 1a shows a schematic cross-sectional view of a plug used in the syringe of FIG. 1 for mixing two components.
Figure 3:
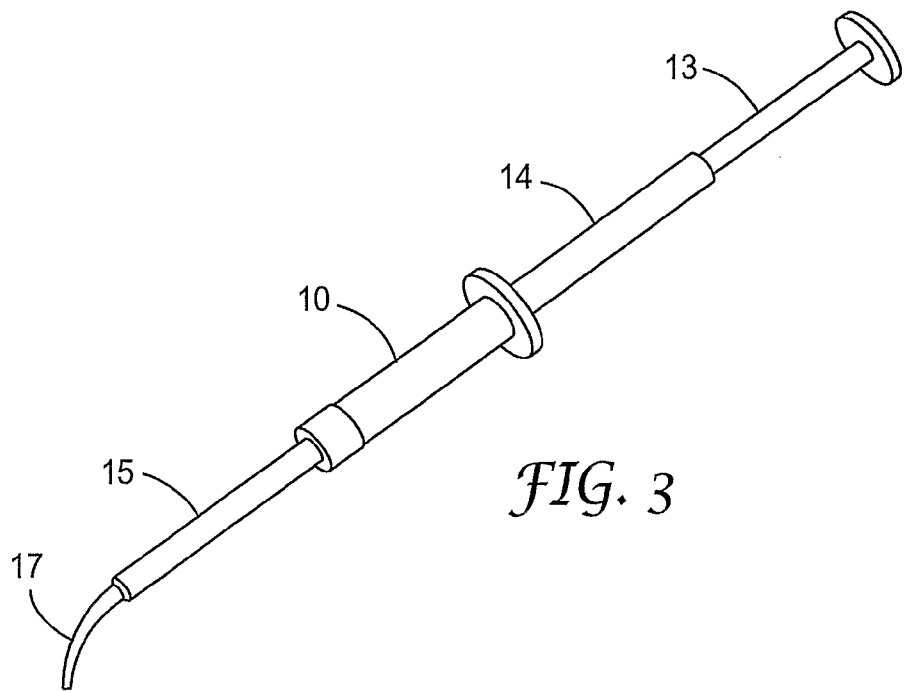
FIG. 3 shows a perspective view of the assembled syringe of FIG. 1.

At the front end of the cartridge 10, the plug 11 is provided. The plug is designed such that it closes both compartments 18, 19 but allows intermixing of the components contained in the chambers 18, 19 upon application of pressure on the plunger assembly 12, i.e., upon movement of the two pistons towards the front end of the cartridge 10. As shown in FIG. 1a, plug 11 preferably comprises a first channel comprising two channel portions 11a and 11b. The first channel connects the first component chamber 18 with the interior of the mixing tip 15. A second channel 11c is provided for connecting the second component chamber 19 with the interior of the mixing tip 15. The first channel is divided into channel portions in order to provide for the necessary closure of the first component chamber 18 prior to the usage of the material. The back end of the plug 11 (right side in FIG. 1a) together with the wall 11d separating the two channel portions from each other closes the first component chamber 18. However, upon activation of the syringe 1, plug 11 is moved towards the front end of the cartridge 10 so that the first and second channel portions 11a, 11b communicate with each other via recess 10b. This is clearly shown in FIG. 1. Material contained in the first component chamber can then flow around the separation wall 11d. Similarly, second channel 11c then provides a flow path from the second component chamber 19 into the mixing tip 15. Prior to activation of the syringe 1, the radial opening of the second channel 11c is covered by the inner wall of the first component chamber 18. Movement of the plug 11 is caused by movement of the inner piston 13 due to hydraulic transmission, for example.

The materials contained in the two compartments are then extruded from their component chambers 18, 19 and mixed by the static mixer 16 due to moving the plunger assembly 12 towards the mixing tip, and the mixture is finally dispensed at the dispensing nozzle 17.

The cartridge 10 is generally formed by two concentric arranged barrels 101, 102 (see FIG. 5) forming the component chambers for storing the paste components, as mentioned above. The inner barrel 101 acts as component chamber for a first paste component, the annular gap 103 between the inner and outer barrel acts as a component chamber for a second paste component. The annular gap 103 may be easily divided into two or more component chambers 103a, . . . , 103n, so as to create a syringe for the respective number of components.

Figure 5:
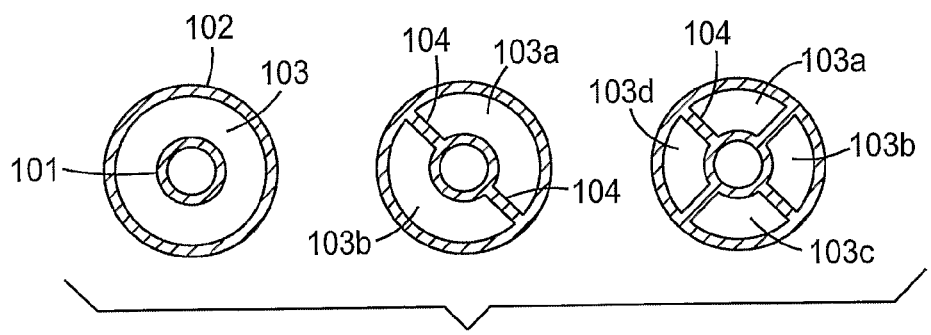
FIG. 5 shows cross-sectional views of three alternative embodiments for dual- or multi-chamber cartridges according to the present invention.
Figure 6:
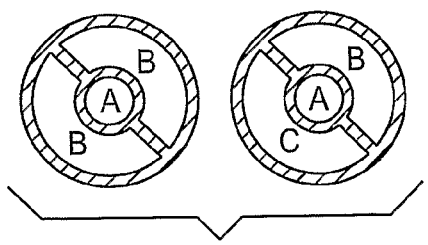
FIG. 6 shows by means of two examples how a three-chamber cartridge can be used for multi-component substances.
Figure 7:
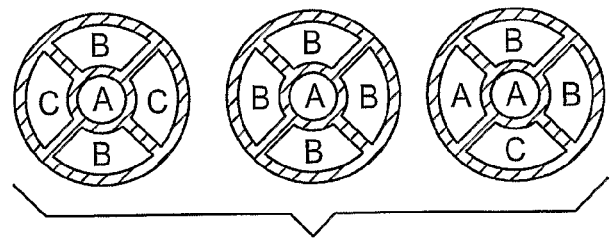
FIG. 7 shows by means of three examples how a five-chamber cartridge can be used for multi-component substances.

The concentric arrangement of the barrels 101, 102 allows a variety of different configurations for the paste materials filled into the syringe. The same cartridge design may be used for materials of different numbers of components: For example, the middle picture of FIG. 5 shows a three-chamber design wherein the two barrels 101 and 102 are connected by two separation walls 104 such that the component chamber 103 is in fact divided into two separate component chambers 103a and 103b. A further alternative embodiment is shown in the right picture of FIG. 5, comprising four separation walls 104 forming four chambers 103a, 103b, 103c, 103d in the gap between the barrels 101, 102. The three-chamber design may be used for a two-component material with components A and B (left picture of FIG. 6), or for a three-component material with components A, B, and C (right picture of FIG. 6). As another example, the five-chamber design shown in the right picture of FIG. 5 may be used for a two-component material (middle picture of FIG. 7; components A and B) and for a three-component material (left and right pictures of FIG. 7; components A, B, and C) as well as for a four-component and a five-component material (not shown). Moreover, such arrangements provide great variability with regard to mixing ratios. For example, the five-chamber design can be used for three-component mixtures with varying mixing ratios. For example, the left and right pictures in FIG. 7 show two different examples for mixtures with components A, B, and C. However, in the left picture, B and C are provided with equal amounts (component A just in the center chamber), whereas in the right picture the amount of A is larger and the amount of C is reduced.

A further advantage of the described concentric multi-component cartridge results from using a two-component paste material with a multi-chamber cartridge, for example a four-chamber cartridge. In this case the components can be arranged in an alternating order so as to achieve premixing via the cartridge design. In this way one mixing element of the static mixer may be saved.

Figure 2A:
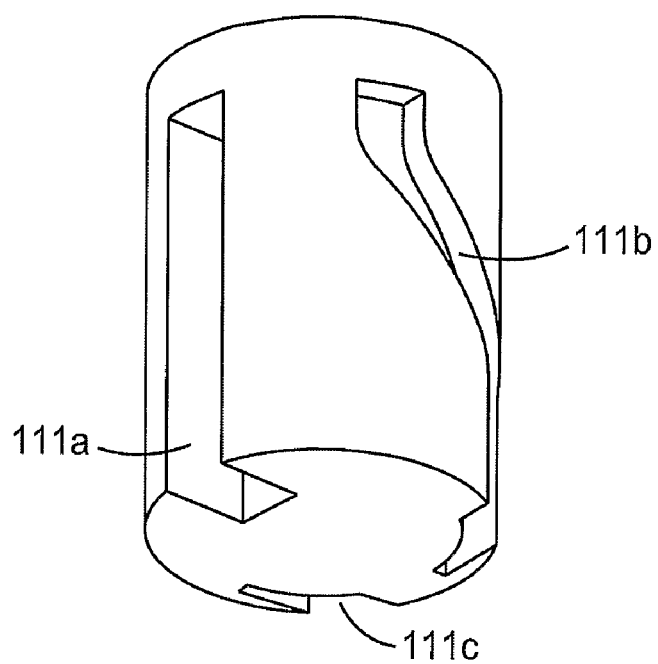
FIG. 2a shows a perspective view of a plug used for mixing three components.
Figure 2B:
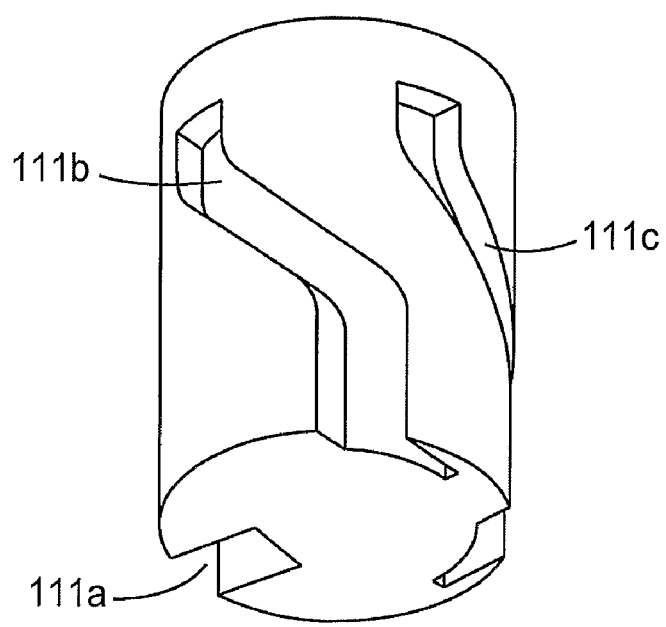
Figure 4:
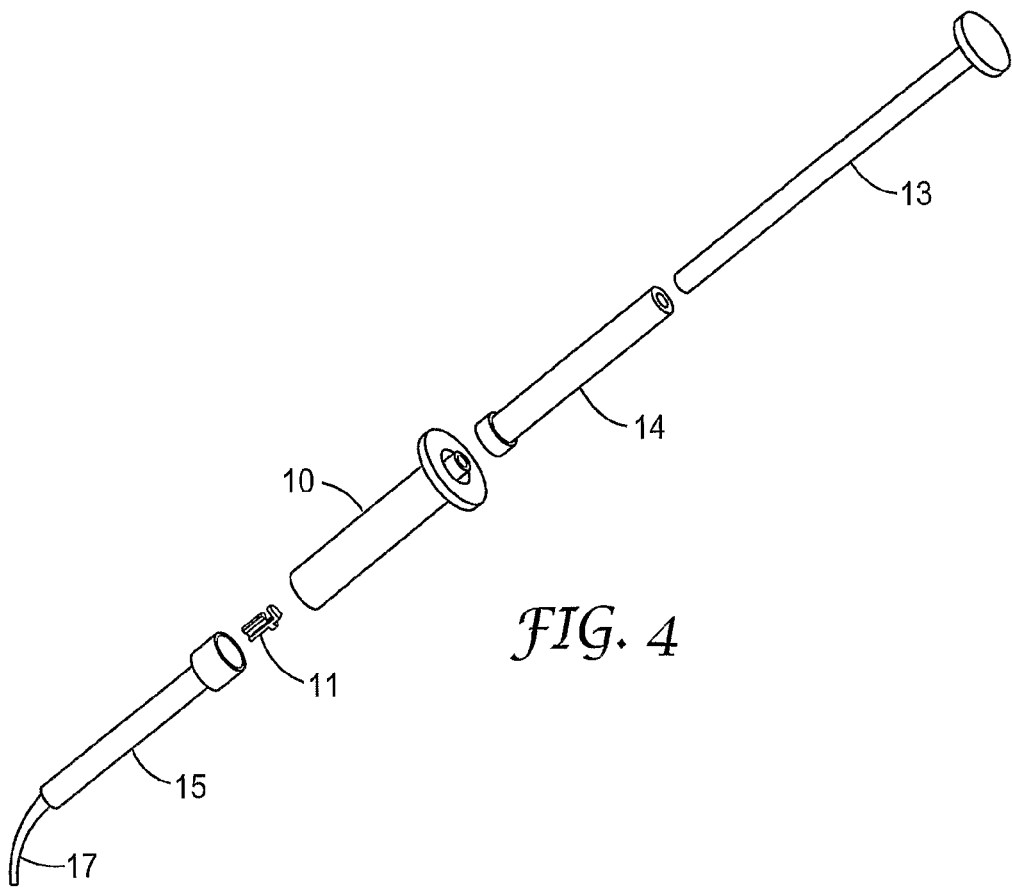
FIG. 4 shows a perspective view of the syringe of FIG. 1 being disassembled.

A plug according to a preferred embodiment for mixing three components is shown in FIGS. 2a and b. A first channel 111a extends parallel to the longitudinal axis of the plug but not along the entire length thereof: it opens to one front surface of the plug but not to the opposite front surface. The second and third channels 111b and 111c are somewhat S-shaped, i.e. the rotational position changes along the length of each channel. The second and third channel 111b and 111c also open to said one front surface but not to the other.

Figure 8:
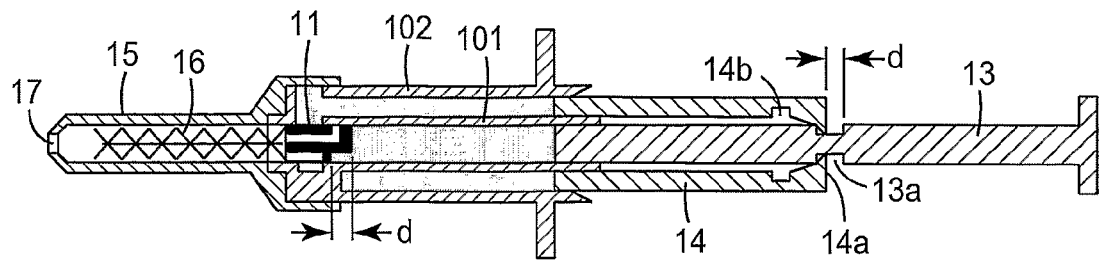
FIGS. 8 to 12 show five different cross-sectional views of the syringe according to the present invention to show the different steps of activating the syringe.

As mentioned above and as shown in FIG. 8, the inner piston 13 comprises an annular groove 13a having a width "d". In the transport and storage condition of the syringe, the engagement projections 14a of the outer piston 14 project towards the center axis of the outer piston 14, i.e., towards the inner piston 13, so that the projections 14a are in engagement with the recess 13a. Moreover, plug 11 is placed in the first component chamber 18 such that both outlets 18a, 19a are closed by the plug 11.

Figure 9:
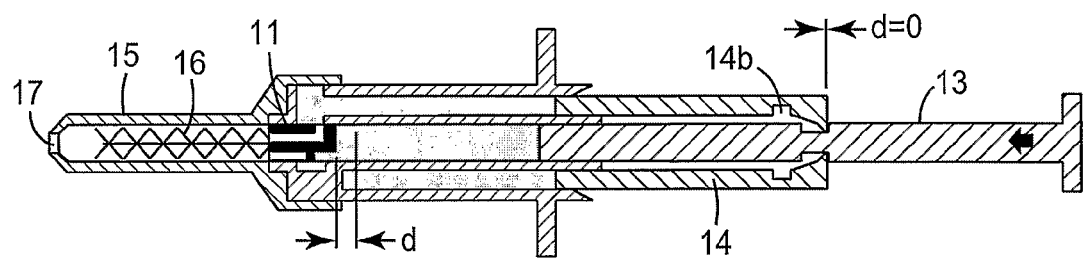

For activating the syringe, the inner piston 13 can be pushed forward over said distance "d" until it links automatically with the outer piston 14 (FIG. 9). At this point, the engagement projections 14a of the outer piston 14 (which does not yet move) abut at the back end wall of the recess 13a. This can clearly be seen in FIG. 9. This short movement over the distance "d" causes the plug 11 to move forward by the same distance "d" thus opening the two chambers 18, 19 containing the paste components. FIG. 9 shows that the plug 11 was pushed (due to hydraulic transmission) forwards so that now the two channel portions 11a, 11b of the first channel are connected via the recess 10b, and the second channel 11c connects the second component chamber 19 with the interior of the mixing tip 15. Thus, according to the present invention, no separate activation step displacing the plug is necessary (like in U.S. Pat. No. 6,613,021). With a single step, i.e. movement of the inner piston 13, the syringe is activatable and the paste can be mixed and dispensed.

Figure 10:
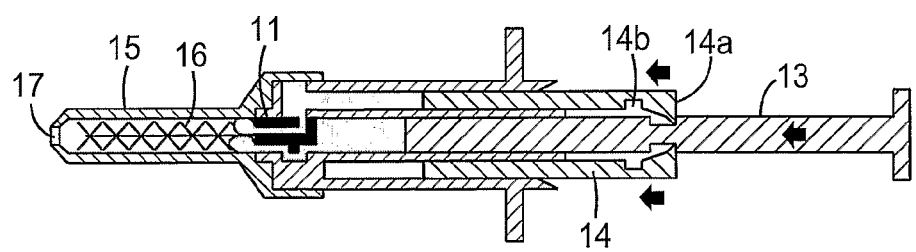

Because of the now existing linkage between the inner and outer pistons, the whole piston assembly 12 moves forward upon displacement of the inner piston 13 (FIG. 10). This way the paste components are simultaneously extruded from the inner and outer chambers. The paste components flow through the flow channels of the plug 11 into the mixing tip 15, where they are mixed, and finally through the dispensing nozzle 17 until the outer piston 14 has reached its end position.

Figure 11:
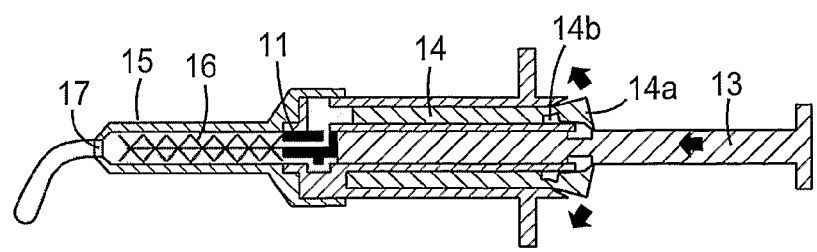
Figure 12:
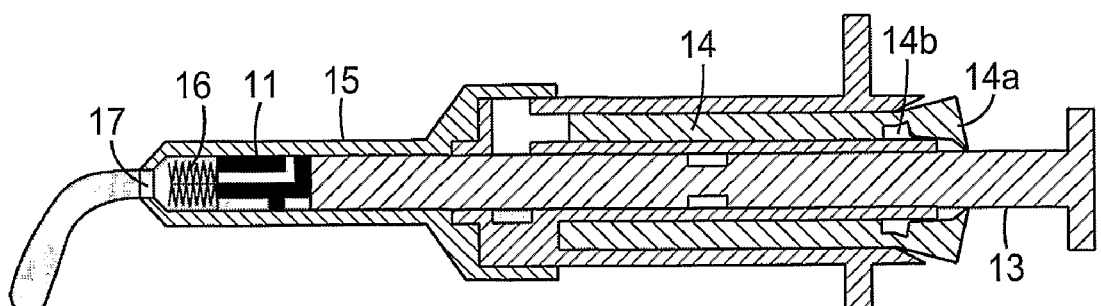

Shortly before or at the same time the outer piston 14 has reached its end position, the linkage or engagement between inner and outer piston is released. This is shown in FIG. 11. The inner piston 13 now moves separately and extrudes the paste still contained in the mixing tip 15 while the static mixer 16 is compressed (see FIG. 12).

Figure 13:
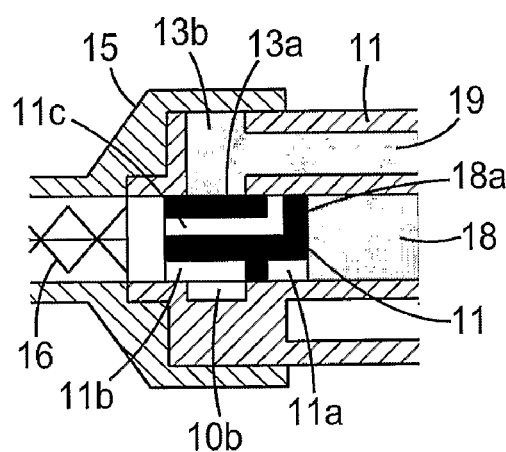
FIGS. 13 to 15 show in detail the plug of the syringe in the closing and the opening position.
Figure 14:
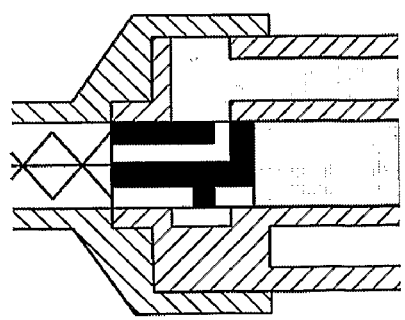
Figure 15:
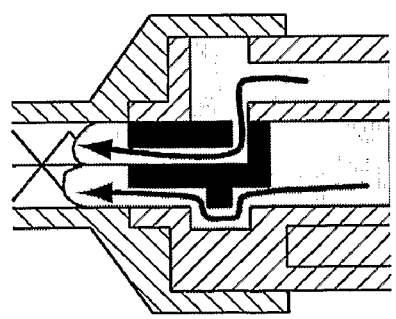

According to the present invention, only one plug 11 may be used as a valve to seal and open the outlets of all paste chambers. If the plug 11, starting from the initial position in which all chambers outlets are closed (see FIG. 13), is displaced by the distance "d" (as mentioned above), the syringe 1 will be activated so that all chamber outlets 18a, 19a are opened (FIG. 14). Then the paste can be extruded through channels (FIG. 15) which are arranged within the plug 11, as indicated by the arrows in FIG. 15.

To achieve activation, extrusion and mixer compression within an all in one movement, a special linkage between the inner and outer pistons is proposed, as mentioned above.

Figure 16:
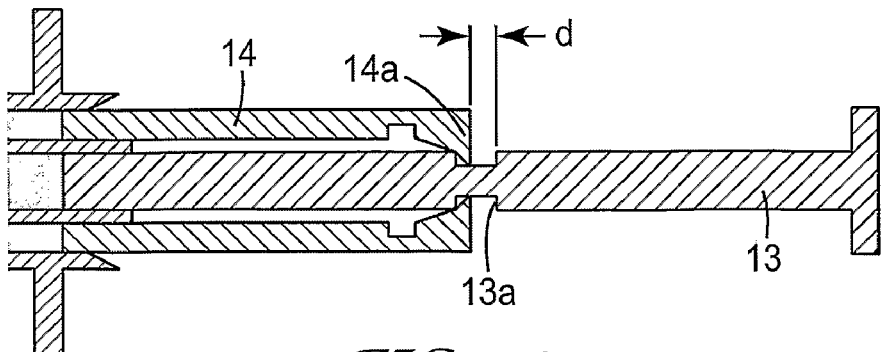
FIGS. 16 to 20 show the engagement (and its release) between the inner and outer pistons of the syringe according to the present invention in detail.
Figure 17:
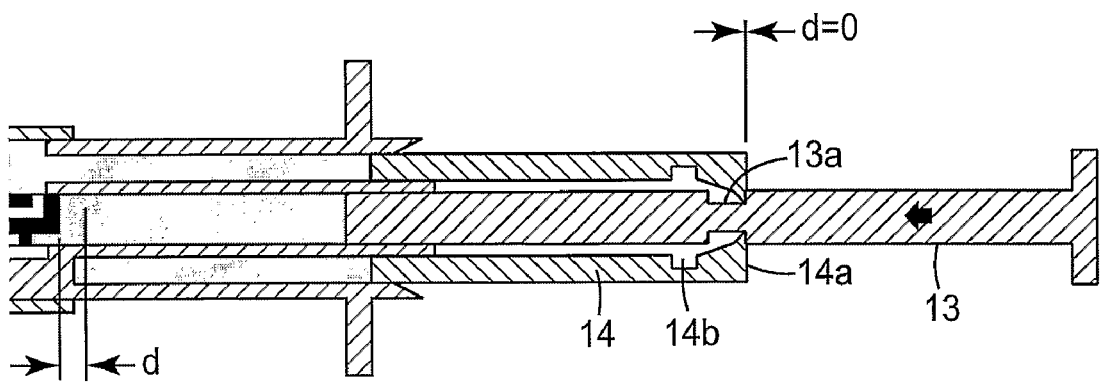
Figure 18:
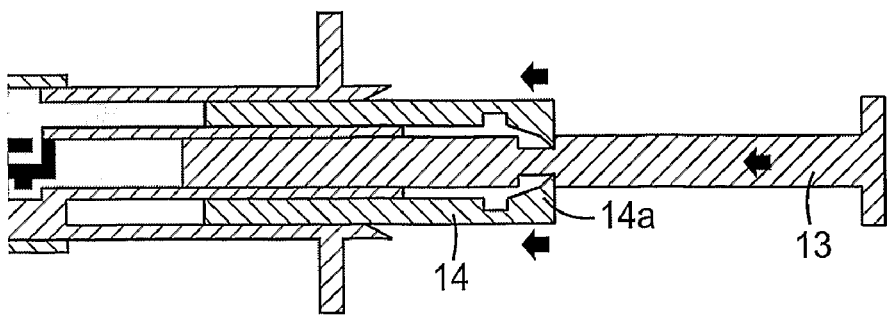

The initial position of both pistons 13, 14 and the position after the syringe 1 has been activated is shown in detail in FIGS. 16 and 17.

The outer piston 14 forms a spring sleeve 14a which engages with the annular groove 13a arranged at the inner piston 13. The annular groove 13a allows the inner piston 13 to be displaced independently from the outer piston 14 by said distance "d" (FIG. 16). When the inner piston 13 is displaced, the paste in the inner chamber 18 as well as the plug 11 are moved forward (FIG. 17). During this step the plug 11 opens all chamber outlets 18a, 19a.

After the inner piston 13 has been displaced by the distance "d" further movement will cause the outer piston 14 to move together with the inner piston 13 (FIG. 18) because of the engagement of the spring sleeve 14a with the recess 13a in the inner piston 13. In this way the paste can be extruded from the inner and outer chambers 18, 19 simultaneously.

Figure 19:
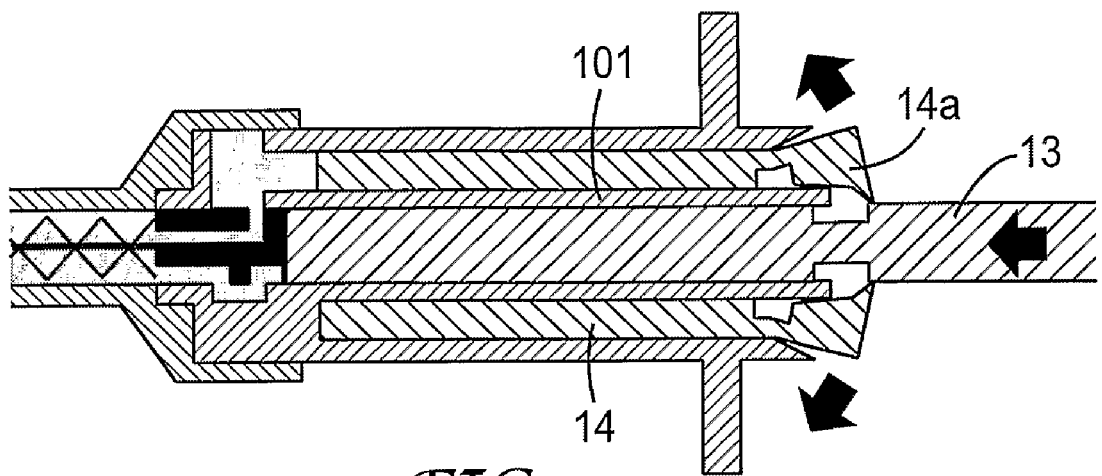

As soon as the outer piston 14 of the piston assembly 12 has nearly reached its final position, the spring sleeve 14a is released from the annular groove 13a (FIG. 19), and the inner piston 13 can be further moved separately. Releasing the spring sleeve 14a is actuated by the inner barrel 101 which penetrates the piston assembly 12 thus displacing the spring sleeve 14a when the piston assembly 12 approaches its final position. In order to release the engagement between the inner piston 13 and the outer piston 14, the back end of the outer piston 14 comprising the spring sleeve 14a is adapted to allow an outward deflection under pressure, as shown in FIG. 19. In the embodiment shown in the Figures, the back end of the outer piston 14 comprises a weakened area such as an annular recess 14b which allows deflection of the projections 14a as indicated by the arrows shown in FIG. 19. In order to facilitate such deflection, the back end of the cartridge 10 is preferably conically shaped (see area 10c in FIG. 1), recessed or just shortened (not shown).

Figure 20:
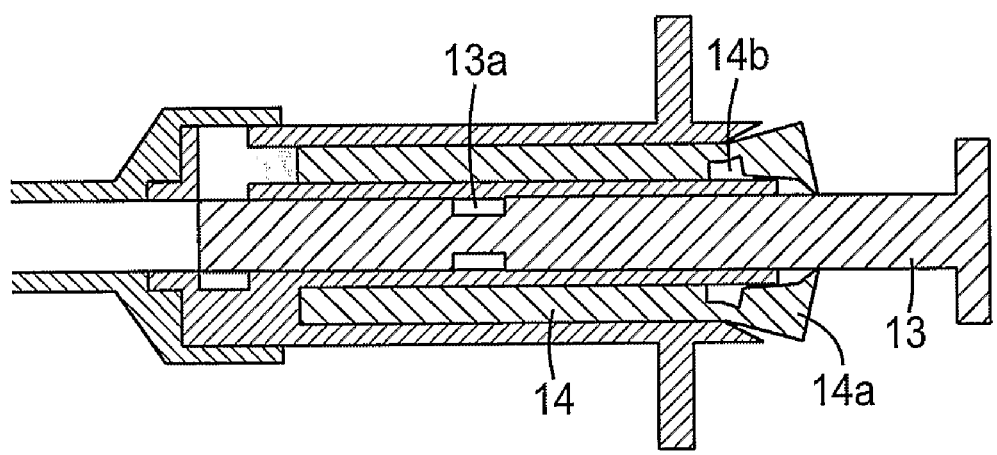

After the spring sleeve 14a is disengaged from the inner piston 13, separate displacement of the inner piston 13 will cause the mixer 16 to be compressed and all the paste to be extruded from the inner barrel 101 and the mixing tip 15 (FIG. 20).

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

The invention claimed is:

1. Syringe for two or more components of a material which are to be mixed together, comprising:
    a first component chamber for containing a first component and at least a second component chamber for containing a second component, each component chamber comprising a chamber outlet;
    a first piston for movement within the first component chamber and a second piston for movement within the second component chamber;
    a plug comprising a first flow channel for the first component and a second flow channel for the second component, the plug being movably arranged in the first component chamber in such a manner that when the plug is in a first position in the first component chamber, the first and second chamber outlets are closed, and when the plug is in a second position in the first component chamber due to advancement of at least one of the pistons, the first and second component chambers are connected via the first and the second flow channels to the outlet of the syringe.

2. Syringe according to claim 1, wherein the first component chamber is concentrically arranged inside the second component chamber.

3. Syringe according to claim 1, wherein the first flow channel is formed by a first channel portion and a second channel portion separated from each other by a separation wall.

4. Syringe according to claim 3, wherein the first and second channel portions of the first channel form a flow path with a first component chamber recess in the second position of the plug.

5. Syringe according to claim 1, the first component chamber comprising at its front end a recess in the inner surface thereof.

6. Syringe according to claim 1, wherein the second chamber outlet is located at the front end of the second component chamber and extends from the second component chamber to the first component chamber.

7. The syringe according to claim 1, said second component chamber further comprising at its front end an inlet from the exterior of the syringe.

8. The syringe according to claim 1, wherein the first piston comprises a recess.

9. The syringe of claim 8, wherein the first piston recess is in the form of an annular recess in a plane substantially perpendicular to the longitudinal axis of the first piston.

10. Syringe according to claim 1, wherein the second piston comprises at least one engagement projection at its back end.

11. Syringe according to claim 10, wherein the engagement projection protrudes towards the center axis of the second piston.

12. Syringe according to claim 10, wherein the engagement projection is formed as a spring sleeve.

13. Syringe according to claim 10, wherein the second piston comprises a weakened area near its back end.

14. Syringe according to claim 13, wherein the weakened area is formed as an annular recess.

15. Syringe according to claim 13, wherein the weakened area allows deflection of the engagement projection.

16. Syringe according to claim 1, wherein a back end of the second component chamber is at its outer edge conically shaped.

17. Syringe according to claim 1, wherein the second component chamber comprises one or more separation walls extending in longitudinal direction of the syringe thus dividing the second component chamber into two or more sub-chambers.

18. Syringe according to claim 17, wherein the second component chamber comprises two or four separation walls equally spaced from each other.

19. Syringe according to claim 1, further comprising a mixing tip comprising a front end with a dispensing opening and a rear end with an inlet opening.

20. Syringe of claim 19, wherein the mixing tip when connected to the component chambers covers the chamber outlet of the second component chamber.

21. Syringe according to claim 19, further comprising a static mixer arranged in the mixing tip.

22. A method of filling a syringe, comprising the steps of:
 a) providing a syringe comprising:
  a first component chamber and a second component chamber, each component chamber comprising a chamber outlet;
  a first piston for movement within the first component chamber and a second piston for movement within the second component chamber; and
  a plug comprising a first flow channel for a first component and a second flow channel for a second component, the plug being movably arranged in the first component chamber in such a manner that when the plug is in a first position in the first component chamber, the first and second chamber outlets are closed, and when the plug is in a second position in the first component chamber due to advancement of at least one of the pistons, the first and second component chambers are connected via the first and the second flow channels to the outlet of the syringe;
 b) filling the first component chamber with the first component;
 c) inserting the plug into the first component chamber from a front end thereof; and
 d) filling the second component chamber with the second component.

23. A method of mixing and dispensing of multi-component paste materials using a syringe, comprising the steps of:
 a) providing a syringe comprising:
  a first component chamber and a second component chamber, each component chamber comprising a chamber outlet;
  a first piston for movement within the first component chamber and a second piston for movement within the second component chamber; and
  a plug comprising a first flow channel for a first component and a second flow channel for a second component, the plug being movably arranged in the first component chamber in such a manner that when the plug is in a first position in the first component chamber, the first and second chamber outlets are closed, and when the plug is in a second position in the first component chamber due to advancement of at least one of the pistons, the first and second component chambers are connected via the first and the second flow channels to the outlet of the syringe;
 b) providing a paste component in each chamber;
 c) activating the syringe and opening the chambers containing the paste components;
 d) extruding the paste components from the component chambers through outlets into a mixing tip containing a static mixer; and
 e) extruding paste remaining in the mixing tip by compressing the static mixer.

\* \* \* \* \*

UNITED STATES PATENT AND TRADEMARK OFFICE
CERTIFICATE OF CORRECTION

| | | |
|---|---|---|
| PATENT NO. | : 7,963,937 B2 | Page 1 of 1 |
| APPLICATION NO. | : 11/570001 | |
| DATED | : June 21, 2011 | |
| INVENTOR(S) | : Helmut Pauser | |

It is certified that error appears in the above-identified patent and that said Letters Patent is hereby corrected as shown below:

Column 3

Line 47; Delete "multicomponent" and insert -- multi-component --, therefor.

Column 8

Line 8; Claim 1, after "and" delete "at least".

Signed and Sealed this
Twenty-ninth Day of November, 2011

David J. Kappos
*Director of the United States Patent and Trademark Office*